United States Patent [19]

Kanitz et al.

[11] Patent Number: 5,782,950
[45] Date of Patent: Jul. 21, 1998

[54] DEVICE AND PROCESS FOR COMPOSTING AND WET FERMENTATION OF BIOLOGICAL WASTE

[75] Inventors: Jürgen Kanitz, Bochum, Germany; Bruno Kesselring, Zizers, Switzerland

[73] Assignee: Beg Bioenergie GmbH, Essen, Germany

[21] Appl. No.: 545,654

[22] PCT Filed: Apr. 19, 1994

[86] PCT No.: PCT/DE94/00440

§ 371 Date: Nov. 29, 1995

§ 102(e) Date: Nov. 29, 1995

[87] PCT Pub. No.: WO94/24071

PCT Pub. Date: Oct. 27, 1994

[30] Foreign Application Priority Data

| Apr. 22, 1993 | [CH] | Switzerland | 1267/93 |
| Aug. 6, 1993 | [CH] | Switzerland | 2360/93 |
| Mar. 19, 1994 | [DE] | Germany | 44 09 539.2 |

[51] Int. Cl.$^6$ ................................................. C05F 11/08
[52] U.S. Cl. ................................................. 71/10; 435/290.4
[58] Field of Search ........................ 71/6, 7, 9, 10; 435/290.4; 425/222; 23/313 R

[56] References Cited

FOREIGN PATENT DOCUMENTS

| 0 172 292 A1 | 2/1986 | European Pat. Off. |
| 40 01 024 A1 | 7/1991 | Germany . |
| 8700306 | 9/1988 | Netherlands . |
| WO 92/15540 | 9/1992 | WIPO . |

*Primary Examiner*—Michael Lewis
*Assistant Examiner*—Stuart L. Hendrickson
*Attorney, Agent, or Firm*—Herbert Dubno

[57] ABSTRACT

Biological waste is squeezed out while being at the same time mixed and homogenized, after which the solid materials freed of liquid are delivered to a composting installation and the liquid fraction is directed to an anaerobic reactor for wet fermentation. Thereby shorter composting and fermentation times can be achieved.

31 Claims, 6 Drawing Sheets

DEVICE AND PROCESS FOR COMPOSTING AND WET FERMENTATION OF BIOLOGICAL WASTE

CROSS REFERENCE TO RELATED APPLICATIONS

This application is a national stage application of PCT/DE94/00440 filed 19 Apr. 1994 and based on the following national applications: German national application P4409539.2 filed 19 Mar. 1994, Swiss national application 2360/93-2 filed 6 Aug. 1993 and Swiss national application 1267/93-7 filed 22 Apr. 1993.

FIELD OF THE INVENTION

The invention relates to a process for treating biological residues, particularly from communal and/or industrial waste materials, including raw and or cooked food leftovers, agricultural waste, particularly animal excrements and/or plant components, wherein the bio-residuals are separated into a solid and a liquid fraction and subsequently the solid fraction is delivered to a silo composting and the liquid fraction to an anaerobic reactor, wherefrom the biogas generated through fermentation is extracted.

The invention further relates to a device for the recovery of biogas or compost through wet-fermentation and composting of organic bio-residues with a reactor for solid materials built as a worm-press type solid-liquid separator, which has a liquid outlet and an anaerobic reactor connected thereto for fermentation with a biogas extraction and a composting installation.

BACKGROUND OF THE INVENTION

In addition to already mentioned waste materials, the concept of bio-residues includes all substances having a content of carbon in dissolved form (DOC) which are capable of fermentation. These can be for instance green vegetable waste, such as long grass, leaves, lawn cuttings, branches, wood cuttings, flowers, horticultural and/or agricultural harvest residues, but also waste from the vegetable and fruit processing industry, such as the peels of fruit, oil fruit, rape, beer sludge, yeasts, coconut fibers, leaves and stems from canneries, potato peels and leaf remnants, bark and chips from wood or paper industries, organic communal or industrial urban refuse and, finally agricultural waste.

It has long been known to compost clean green residues by storing the comminuted residues with or without composting additives in compost piles and left to rot, whereby the waste was slowly decomposed. In the meantime it became known that the rotting time can be shortened by shuffling the stacks piled up in layers, as well as by to concerted process control with monitoring the temperature and/or stack humidity.

In the EP 0 429 744 A2 a process is described wherein the waste material, after being pretreated by sifting, separating and comminuting is fed to a fermentation tank, where it is slowly pushed towards the central exit opening while being continuously stirred, in order to induce and maintain an aerobic biological decomposition process. In order to improve this fermentation method an aerobic biological rotting of biological waste is provided, whereby the waste is intimately mixed with air by to continuous stirring and is then subjected to a bacterial aerobic decomposition, and the product resulting from the rotting process is removed from the receiving tank and subjected to purification. For this purpose approximately half of the receiving tank has to be filled with solid waste with subsequent addition of liquid substances and agitated over a residence time of 2 to 3 hours, prior to adding decanted slurry and white lime and the stirring has to be continued for a residence time up to 69 or 70 hours.

WO 92/15540 describes a process for separate treatment and disposal of mixtures of solid and liquid organic waste materials, whereby the mixture is split by mechanical separation into a liquid phase with a low content of finely distributed solids and into a solid phase with a water content, after which the liquid phase undergoes an anaerobic fermentation process with generation of biogas, and the solid phase undergoes an aerobic fermentation process to form compost, fertilizer or fodder. The ballast substances present in the biogas and/or the liquid phase are removed by chemical means, such as precipitation, or flocculation and conveyed to the cycle before the biogas is burnt, or the liquid phase is discharged into a clarification basin or fed to subsequent purification. This process can be applicable to liquid manure from pigs and cows, slurry, whey or similar substances. For the mechanical separation into a liquid phase and a sludge, a standing screen-centrifuge, a horizontally positioned worm-press separator with a sieve and a decanter are proposed.

The EP 0 172 292 A1 relates to a process for treating organic liquid waste, whose solid fraction is separated and fed to an aerobic fermentation, while the liquid fraction is subjected to anaerobic fermentation. In any case the carbon-containing waste such as wood remnants, manure, bark, fruit peels, saw dust etc. On the one hand and food leftovers on the other hand, as well as finally solid materials from a drum sieve which serves for the separation of solid-liquid mixtures are delivered to a comminuter, before they are fed as a semisolid bulk to form compost. In this process also only the part of liquid already present in the solid-liquid mixture is used.

OBJECT OF THE INVENTION

It is the object of the present invention to provide a process of the above-mentioned kind and a device, for an improved treatment of organic residues for the production of usable substances, such as compost and/or biogas.

SUMMARY OF THE INVENTION

The process for treating organic bio-residues particularly from communal and/or industrial waste including raw and cooked food leftovers, agricultural waste, particularly animal excrements and/or plant components, comprises steps wherein the bio-residuals are separated in a solid and a liquid fraction and subsequently the solid fraction is fed to an aerobic silo composing and the liquid fraction is fed to an anaerobic reactor from which the biogas generated during fermentation is extracted. According to the invention the c-containing (organic) components dissolved or soluble in water are washed out from the bio-residues prior to the solid-liquid separation, under intensive mixing and homogenization.

Due to the separation of the waste in a liquid fraction and a solid fraction, which is available as a suspension resulting from sifting, an aerobic treatment of the solid fraction on the one hand and an anaerobic treatment of the dissolved and suspended fraction can each be better controlled, whereby especially tanks with smaller volumes are required than in a common treatment of both fractions. Comparatively the separated composting and wet fermentation can altogether take place quicker in the production of valuable high-quality final products.

For instance in the separating stage, wherein after feeding the waste a moisture contact of 70 to 80 % by volume is present, this humidity level is maintained, which is possible even after the liquid suspension is discharged, by to the addition of water, e.g. process water. The humidity level in the separation stage should at least not fall below 40 to 60 % by volume, since only in the presence of relatively high humidity it is possible to wash out the C-containing components. Preferably the process water is fed to the separation stage after recycling, from the methanization (fermentation) stage in the anaerobic reactor.

A further improvement of the process control in the separation stage can be achieved due to the concerted, controlled air supply and temperature control, particularly by maintaining a constant temperature. The respective adjustment can be made depending on measured temperatures, oxygen contents, $CO_2$-contents in the waste gas, etc.

Solid fractions still contained in the liquid which reach the anaerobic reactor, are extracted as slurry from time to time, whereby small amounts of metals, particularly heavy metals can be eliminated, by being first dissolved and later precipitated out in combined precipitates.

In the anaerobic reactor during the entire methanization process a temperature of 45° C. to 40° C. is maintained in the treatment with mesophilic bacteria and of 50° C. to 55° C. in the treatment with thermophilic bacteria. The filling of the anaerobic reactor with the liquid discharge from the separating stage takes place continuously or at intervals of 1 to 2 hours. The hydraulic residence time ranges approximately between 8 to 10 days at a decomposition rate of the organic substances of 90 to 95 %. This dwelling time in the anaerobic reactor short by compared to the conventional processes, has the following reasons.

According to the invention the organic substance to be methanized is already available in a form accessible to the methanogen bacteria, furthermore it is possible to counteract in a targeted manner the washing away of the bacteria. At a decomposition rate of more than 90 % only slightly charged water leaves the anaerobic reactor. The content of organic matter dissolved in water (DOC content) can be automatically surveyed by means of corresponding devices installed on the reactor.

Optionally the water can be led in a cycle when the DOC contents are (still) too high, i.e.it is returned to the anaerobic reactor until the fermentation is completed.

The apparatus for implementing the process has a reactor for solid materials with a mixing mechanism and a liquid discharge and a subsequently arranged anaerobic reactor for fermentation with biogas extraction or a composting installation. In order to prevent the transport through the worm conveyor from being impeded by the biological waste materials coming from above, a table, respectively table plates are arranged at an angle above and parallelly to the worm press. The supplied material can fall on them and slide downwards, so that once arrived there it can again be seized by the worm and conveyed upwards. Depending on the purpose, i.e. whether the emphasis is on production of biogas or on the preparation of compost, in addition to the separation stage, alternately or next to each other, an anaerobic reactor and/or composting installation can be subsequently arranged. For the time being the production of biogas is of paramount importance, while the use of compost is limited to few fields and can be hardly performed economically.

The mixing device for the acceleration for the pressing or separating of the solid materials from the liquid materials which absorb the carbon in dissolved form, consists of a worm press, preferably of two oppositely-running, inclined worm presses. These worm shafts working in opposite directions lead to an intensive mixing of the biological waste and insure a uniform oxygen supply and thereby an optimal microbial activity. Preferably the worm presses work approximately 5 to 10 minutes per hour. Since the worm presses have an inclined position, the material can be conveyed upwards.

According to a further embodiment of the invention the table or the table plates are designed as heat exchangers. This creates advantages because the material conveyed through the worm presses comes each time in contact with the table, and because the table can be relatively centrally arranged with respect to the material flow.

In order to prevent solid materials of a larger diameter from being discharged together with the liquid, the reactor for solid materials has at least one screen, preferably several punched screens or slotted hole screens arranged on top of each other with various mesh widths, which are arranged upstream of the liquid discharge. For instance three superimposed screens can be used.

According to a further embodiment of the invention the reactor for solid materials has a gas evacuation device, which preferably is connected with a compost filter, so that the escape of smells into the environment can be avoided.

Depending on the composition of the biological waste fed to the reactor for solid materials, it can promote the separation process when the angle at which the reactor for solid materials is positioned, i.e. especially the bottom inclination of the reactor, is changeable.

According to a further embodiment of the invention the reactor for solid materials preferably has a closable feeding funnel and a troughed chain conveyor which preferably is gastight and/or is provided with active air exhaust by means of lateral channel fans. The aspired air can also be pushed through a deodorizing compost filter, in order to avoid smell emissions as much as possible.

As already mentioned above between the reactor for solids and the anaerobic reactor a sedimentation tank is provided, which according to a further embodiment of the invention has an outlet through which the resulting sludge is discharged and can be directly delivered again to the reactor for solid materials. Particularly the reactor for solid materials and/or the sedimentation tank can be equipped with a ventilating cycle or an air supply device, in order to convert the discharged sludge into an aerobic, activated sludge.

In order to operate the anaerobic reactor practically free of oxygen, between the sedimentation tank and the anaerobic reactor a degassifying reactor, preferably an ultrasound reactor or a biostripper, is provided.

The anaerobic reactor is built as a packed bed reactor and/or has several grid supports with large surfaces (150-300 $m^2/m^3$) promoting growth on the surface, which according to another embodiment of the invention have a rough surface. This effectively prevents a washout of the bacteria, further improving the speed of the growth on the surface.

In the anaerobic reactor at first acetogen bacteria convert the dissolved intermediate products into acetate, hydrogen and carbon dioxide. This is necessary since the methanogen bacteria can produce methane only by starting from these products. In the final stage of the biogas production, due to the methanogen bacteria on the one hand methane and water is formed from hydrogen and carbon dioxide and on the other hand carbon dioxide is formed from acetate and methane. The first reaction is catalyzed by hydrogenotrophic methanobacteria, the second by acetotrophic bacteria. The methane yield reaches approximately 70 % by volume. A limiting factor in the anaerobic fermentation is the relatively slow growth of bacteria. i.e. a doubling takes place only every 14 days. Therefore it is necessary to insure a stabilization, or an increase of the microorganism population through growth on the surface on the grid supports, whereby a rough grid surface increases the surface growth of the bacteria, by maintaining a lumen required for the rising of the gas bubbles. A reduction of the bacterial population due to washout can be considerably minimized in any case, whereby the dwelling time in the anaerobic reactor is substantially shortened the reactor volume can be selected to be correspondingly smaller.

According to a further embodiment of the invention the anaerobic reactor has a gas dome, which is preferably connected with a gas separator to which the gas is directed with a slight underpressure.

The anaerobic reactor as a methanization stage can consist of several segmented packed bed reactors arranged one after the other and connected to each other by communicating pipes. The water transport takes place according to the principle of communicating pipes solely via the inlet into the first packed bed reactor. For instance the packed bed reactors can be cylindrical tubes of 4 m height and 1.2 m in diameter, each of them being supplied in the downflow modus. The last packed bed reactor can be succeeded by a sedimentation tank.

According to a further development of the invention the pH-values can be set to be different and independently of each other in different packed bed reactors and/or the different packed reactors can be operated in parallel or in series. There is also the possibility of combined forms, so that for instance two packed bed reactors are connected in parallel, while one of them is connected in series to a third. Advantage can be taken of these variants, so that in different reactors different processes are carried out, optionally with different dwelling times.

According to a further embodiment of the invention the packed bed reactor (anaerobic reactor) is output-controlled, namely preferably via the discharged gas volume (biogas), the DOC and/or the CSB content. Further connection variants can be provided with regard to the heating, somewhat in the fashion that the anaerobic reactors are successively heated with one and the same heat exchanger.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
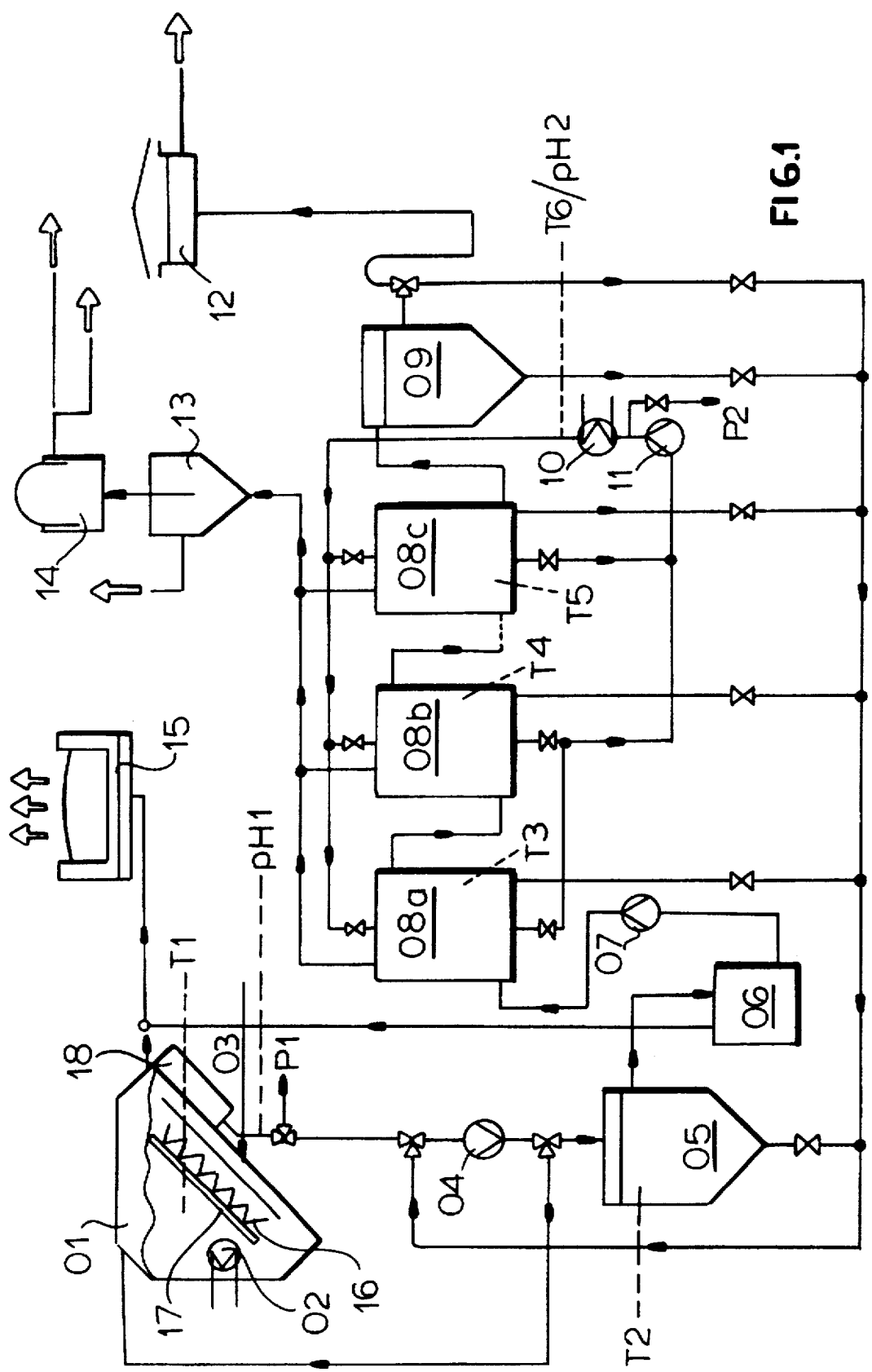
FIG. 1 is a flow diagram of the device of the invention.

The essential parts of the device are the solid-materials reactor 01, as well as the anaerobic reactor consisting of three parts 08a, 08b and 08c, which form the heart of the entire installation. The biological residues or waste materials to be treated are fed to the reactor 01 for solid materials, where in the lower part of the reactor they are seized and moved upwards by a worm shaft 16 or two worm shafts working in opposite directions (see FIGS. 3, 4). In the upper area, i.e. above the compression zone with a slotted hole screen the moisture is squeezed out and expressed from the reactor via the slotted hole screen. Above and parallel to the worm or the oppositely working worm shafts a table or table plates 17 are arranged, which are designed as heat exchangers 02. The squeezing effect on the biological waste materials can be enhanced by the counterpressure of the table plates, as well as due to a distance between slotted hole screen and the worm shaft which decreases towards the discharge. Optionally this distance can also be modified by adjusting the point of rotation at the expressing or emptying device 18. Since the slot width of the screens can not be changed, the screens are replaceable and therefore adjustable to the respective requirements of the biological residues to be processed. The waste materials freed of excess moisture are pressed into the free reactor space by the continuously following conveyed material coming from the screen and compression zone. Thereby due to gravity they slide again back over the table plate towards the deepest part of the reactor 01 for solid materials, where they are again seized by the worm shafts 16. In this manner the waste materials run in a close circuit and can be continuously relieved of the excess moisture and the carbon dioxide contents of the waste material can be washed out by the available liquid. The reactor for solid material has a controlled oxygen supply 03 in order to insure optimal microbic activity. The oxygen supply can be measured, respectively adjusted, based upon oxygen-content measurements or $CO_2$- concentration measurements. During the aerobic intensive rotting which takes place in the reactor 01 for solid materials, energy rich polymer substances, such as fats, proteins and carbohydrates are decomposed in energy poorer monomer components, such as fatty acids, aminoacids and sugar. The duration of the preceding aerobic intensive rotting which takes place in the solid-material reactor 01 is variable and depends on the intended purpose, whether more biogas or more compost is to be produced. For instance during a 48-hour dwelling time in the reactor 01 for solid materials, the light and medium-heavy decomposable organic substances can already be split into low-chain fatty acids and alcohols, and these can be anaerobically decomposed further in the anaerobic reactor 08a, 08b and 08c into the main final product methane and carbon dioxide through acetogen and methanogen bacteria. The fatty acids and alcohols are dissolved and suspended in the water resulting during the conversion, which is available due to the natural humidity or bound in the cell water and squeezed out. The suspension with high contents of aerobically hydrolyzed organic substances is separated over the mentioned screen from the mass in the solid-matter reactor 01. After the extraction of the soluble organic components together with the aerobic intensive rotting a strong volume reduction of the material (70 to 80 % by volume) occurs. The suspension obtained from the biological waste is transported via a valve P1 through the pump 04 into a sedimentation tank 05. The therein separated solid materials which precipitate as sludge can be pumped back as inoculum into the biological waste freshly introduced in the reactor 01 for solid materials. The water freed of solids and enriched with materials with organic content, especially carbon content, is pumped into the anaerobic reactor 08a–08c. The remaining washed-out solid mass is subjected as fresh compost with a rotting degree I and II to a subsequent rotting in the form of a silo composting. The fresh compost is carried off.

The filling of the reactor for solids takes place through a closable opening in the top portion of the reactor, which is opened only during filling. The evacuation of the fresh compost takes place over a discharge sluice actuated by an electromotor. The material falls into a closed container (not shown in the drawing.

In order to avoid odor emissions the reactor for solid materials is connected to a compost filter 15 via a gas line. While in operation the reactor for solid materials remains closed, preferably gastight. The air blown into the reactor for generating aerobic conditions leaves it only through the compost filter. When the reactor is opened for charging, a side channel fan mounted in the gas line starts automatically to aspire air from the reactor in the compost filter. Thereby an inversely directed air flow is created, so that an odor emission from the reactor 01 for solid materials can not occur.

In order to insure that the suspension freed of solid substances or wherein solid substances have been reduced to a minimum, does not introduce any oxygen into the anaerobic reactor 08a–08c, an ultrasound degassing device 06 is provided, through which the liquid is directed and then finally reaches the anaerobic reactor 08a–08c by means of a pump 07. The multiple stage anaerobic reactor 08a–08c, which can be operated in cycle by means of communicating pipes, is fitted as a packed bed reactor. A further sedimentation tank 09 is provided downstream of the anaerobic reactor 08a–08c, through which the water still containing minor solid particles after methanization is guided and freed of solids. Subsequently the water can be redirected into the circuit, in a recycling manner. The anaerobic reactor has a heat exchanger 10 which preferably is connected via a corresponding control with the heat exchanger 02, so that the heat resulting from the exothermic reaction in the reactor 01 for solid materials can be directed into the anaerobic reactor 08. The pump 11 assists circulation of the liquid through the stages 08a–08c.

The water leaving the anaerobic reactor 08a–08c, with a DOCcontent of 1g/l and a CSB-content of approximately 2 to 3 g/l, is directed to a plant clarification installation 12 and is there purified to drainage quality. The clarification installation is a multiple layer packed-bed filter with vertical throughflow, populated by helophytes and equipped with automatic interval operation. This packed-bed filter is characterized by its origin of aerobic bottom layer with a permeability coefficient (Kf) of $5 \times 10^{-3}$ ms. In this layer the nitrification of nitrogen and especially the oxidation of the remaining organic substances dissolved in the water take place. The succeeding dense soil layer with a Kf-value of $10^{-7}$ m/s favors a denitrification of the nitrogen, which can escape into the atmosphere as $N_2$ through a corresponding duct. Due to the higher fine grain fraction a high phosphate binding potential is insured. The permeability of the lower layer corresponds to the one of the upper layer. What results is a residual mineralization of the organic substance, a nitrification of available N-components and to a further reduction of the germination index.

Test have shown that this system with vertical throughflow of the plant clarification installation meets the criteria set for water of drainage quality, even falls below these requirements.

Over the root system of the reed (rhizome) the draining effect is constantly insured. The stems shadow the bottom body and prevent undesired algae formation. They afford a favorable climate for microorganisms. An important property of the plants consists in the capability to introduce oxygen into the soil through a special air conductive tissue (aerenchym). The installation is lodged on a surface of 6 m×5 m. The water drainage of the installation is captured and held for one week. The decision whether to discharge the water into the drainage or to direct it to a clarification basin is made only after the analysis of the water as to the parameters according to indirect introduction regulations.

The biogas formed in the anaerobic generator reaches via a gas separator 13 the gas storage 14 which serves as a buffer for compensating the quantity fluctuations in the production of biogas, in order to insure an even supply to the subsequently arranged gas motor. Here a Sterling motor can be used.

The compost filter 15 which can receive odor-loaded exhaust air from each process stage consists preferably of a special compost layer packed in a 2.5 m annular shaft, in the bottom up to the upper rim. The gas to be deodorized is guided into the filter from the bottom. It flows through the compost layer. Substances with an active odor are adsorbed or absorbed and are metabolized by microorganisms. The gas leaving the filter is normally almost neutral from the odor point of view or it has a slightly earthy smell, which however can be perceived only immediately above the filter. The exhaust air is free of possible pathogenic germs, which possibly have been introduced with the waste in the reactor 01 for solid materials.

Figure 2:
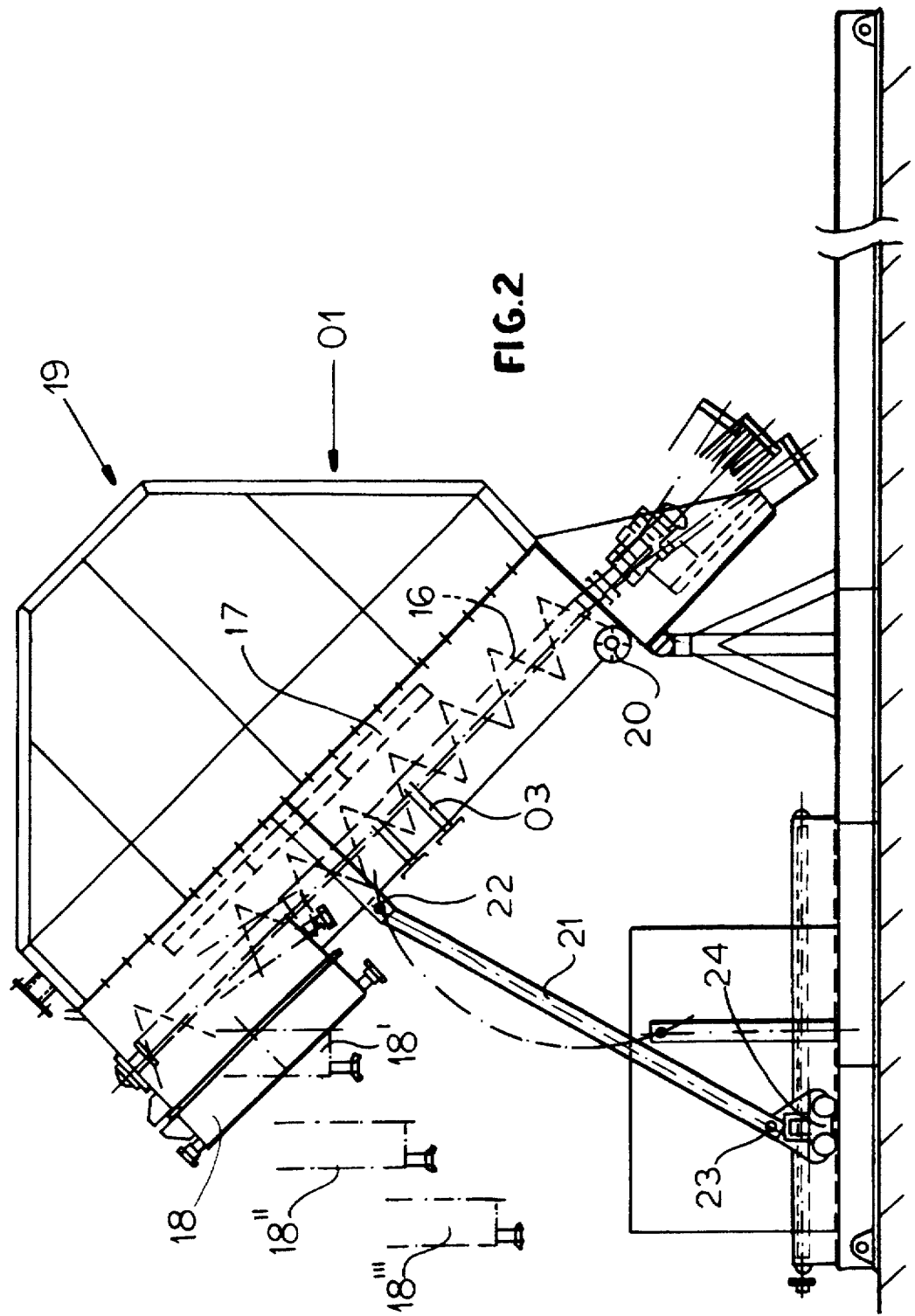
FIG. 2 is a schematic lateral view of the reactor for solid materials.
Figure 3:
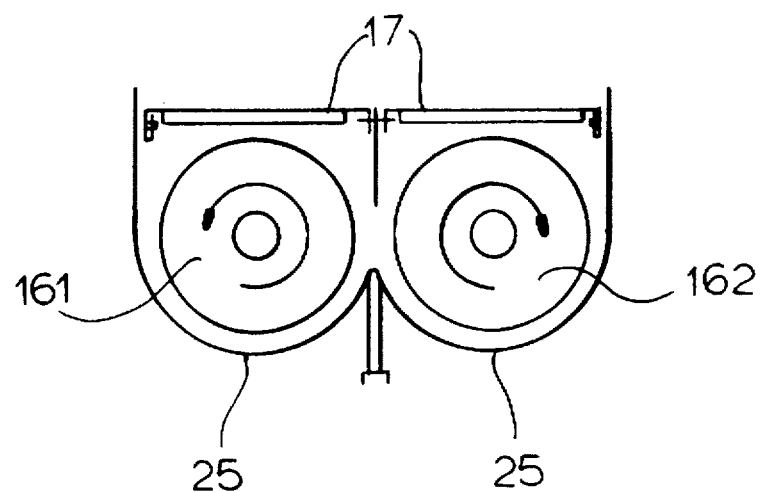
FIG. 3 is a first cross-sectional view of the worm conveyor at the level of the guide plates arrangement.
Figure 4:
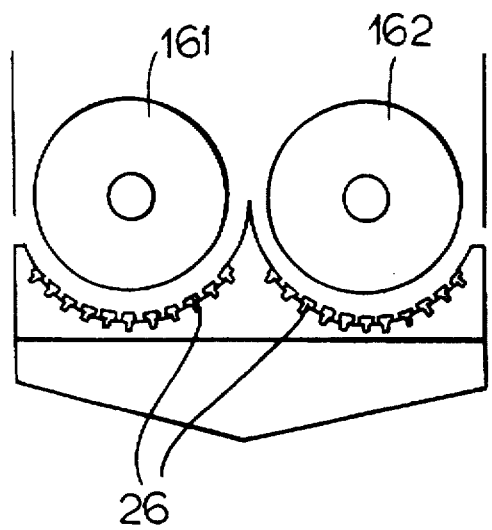
FIG. 4 is a further view of the worm conveyor at the level of the slotted hole screen.

In FIG. 2 to 4 details of the reactor for solid materials can be seen. The reactor for solid materials has an upper charging opening 19, which is opened only for charging and during the remainder of the operation is closed off as gastight as possible. The reactor 01 for solid materials is linked to a first rotary axle 20 and it can be raised and lowered via a swivel arm 21 so that it can be set at various angles of inclination. On the one hand the swivel arm 21 is connected via an articulation 22 with the reactor 01 for solid materials and on the other hand with a rolling truck 24 via a further articulation 23. For mixing and homogenization the reactor for solid materials has at least one worm shaft 16, preferably two worm shafts 161 and 162 working in opposite directions, as can be seen from FIG. 3 and 4. Above the worm shaft a table 17 built as a heat exchanger is arranged. In its upper area the reactor for solid materials has a squeezing and emptying device 18, which can be swung approximately into the positions 18', 18 " and 18'" and which makes possible the discharge of the reactor for solid materials, when the biological waste is completely washed and squeezed out. The worm shafts 161 and 162 are arranged in shells 25 (FIG. 3).

In the upper area of the emptying device 18, i.e. approximately in the upper third of the reactor for solid materials a slotted hole screen 26 is provided in the shells, whereby the slotted holes run parallelly to the conveying direction and/or the slotted hole screen can be at a decreasing distance from the periphery of the rotating worm shaft. Advantageously the distance between the slotted hole screen and the conveyor worm, as well as the contact pressure, are changeable.

It can also be provided that the conveying direction be changed above the squeezing zone due to the modification of the worm winding, thereby achieving an increased squeezing effect.

Optionally the solid-material reactor has at its lowest point reclosable outlet openings for liquid, respectively suspension.

In order to prevent clogging in the conveying area, flexible devices such as brushes, rubber bands or stripping elements and the like can be provided, which clean the conveyor worm, respectively worm shafts.

Figure 5:
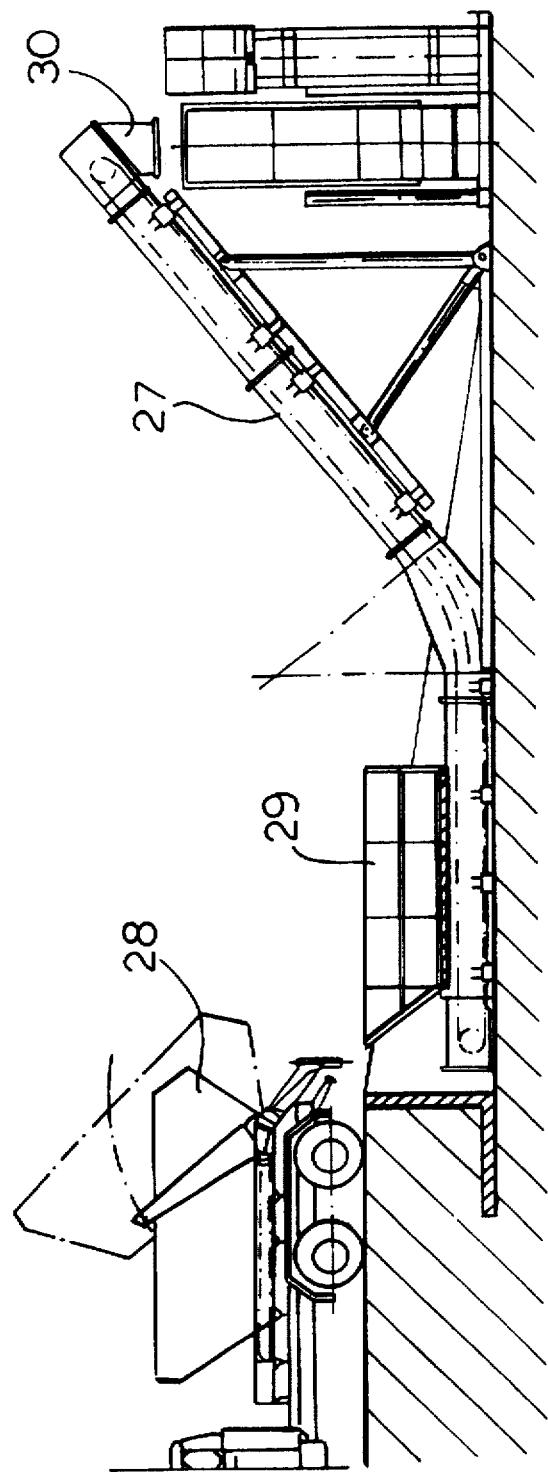
FIG. 5 is a schematic side view of the troughed chain conveyor with the packed bed reactor.
Figure 6:
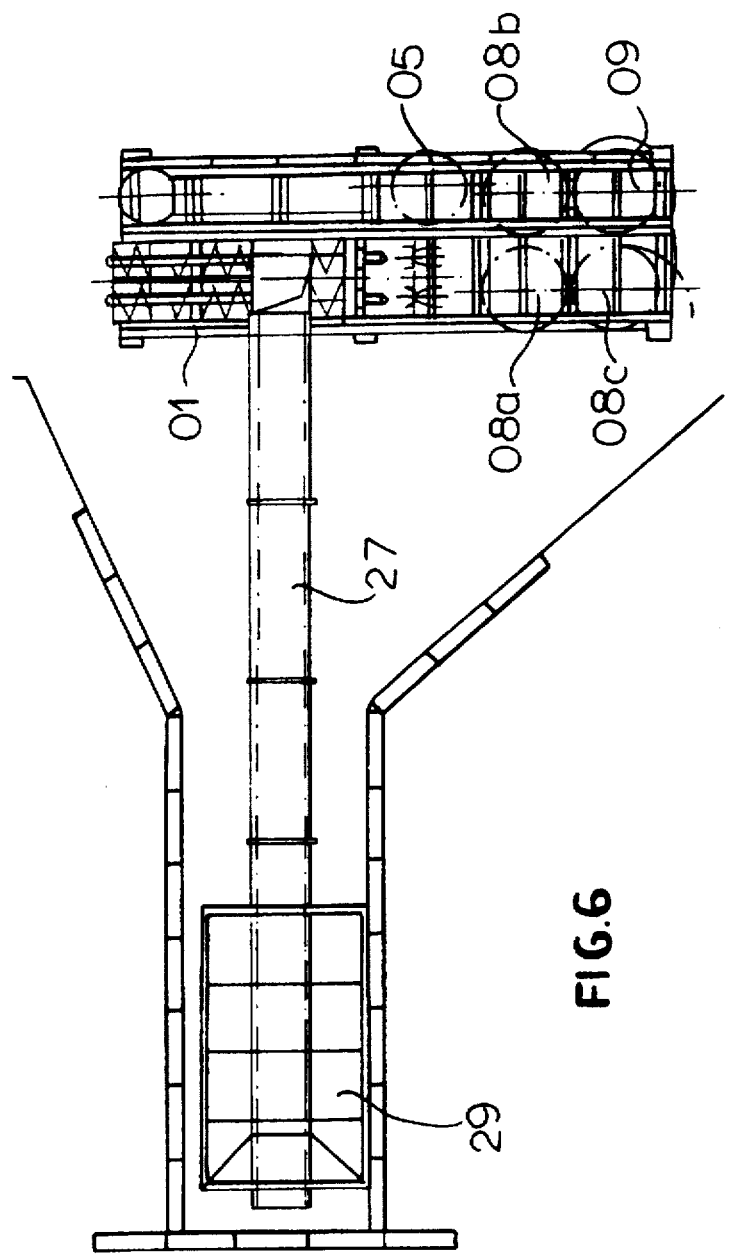
FIG. 6 is a top view of the arrangement according to FIG. 5.

FIG. 5 and 6 show suitable expansions of the device previously described. Upstream of the reactor 01 for solid materials a troughed chain conveyor 27 is suitable arranged. The troughed chain conveyor is charged by a container vehicle 28 which transports the biological waste into a feeding funnel 29. The waste is transported in a closed cage to the discharge 30 which is located above the filling opening 19 of the reactor O1 for solid materials. Excess material which can not be directly introduced in the reactor 01 for solid materials, remains in the conveyor until the next possible filling operation. The filling funnel 29 is opened only during the charging operation, in order to avoid odor emissions. Outside these times the system is closed with a braced tarpaulin. The discharge of the conveyor is also closed off by means of a slidable plate or a slide gate; the conveyor trough is also gastight. Optionally the troughed chain conveyor can be equipped with an active air exhaust which aspires air from the conveyor during operation as well as outside the charging operation at set intervals, by means of a side channel fan and guides this air towards the compost filter 15 for deodorizing.

The filling funnel 29 of the troughed chain conveyor 27, as well as the conveyor itself constitute the intermediate storage for the delivered biological waste. The resulting infiltration water is afterwards kept in the conveyor and directed into the reactor 01 for solid materials or to the subsequently arranged sedimentation tank 05.

As can be seen from FIG. 6 in a top view of the represented embodiment example the reactor 01 for solid materials is elongated. In the immediate vicinity of the reactor 01 for solid materials there is the sedimentation tank with a gas volume of approximately 3 m$^3$, as well as the anaerobic reactor 08a–08c, consisting of three segmented packed-bed reactors 08a, b and c arranged one after the other, each with a chamber volume of 4 m$^3$ in cylindrical pipes with a height of 4 m and a diameter of 1.2 m. The packed-bed reactors 08a–08c, can be operated at a total load per volume up to 35 kg OTS/m$^3$xd. The three reactors 08a, 08b and 08c are succeeded by a fourth pipe functioning as a sedimentation tank 09. The pipes 08a, b and c and 09 form a unit and are installed on a base surface of 2.7 m×2.7 m and completely insulated.

Figure 7:
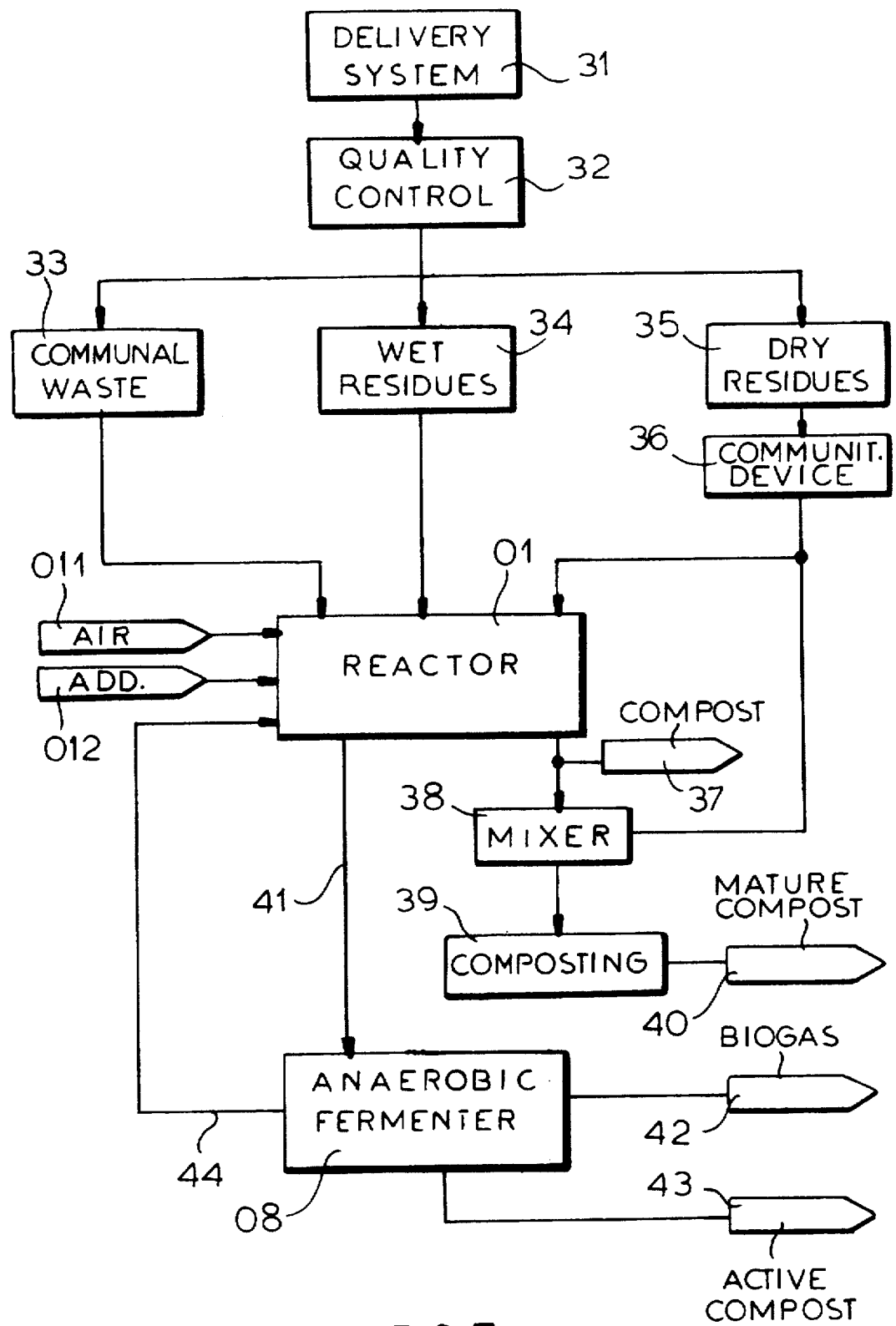
FIG. 7 is a flow diagram of the process according to the invention.

The process of the invention illustrated by the flow chart according to FIG. 7 is implemented by means of the described device. After the delivery system 31 and quality control 32 for the delivered biological waste, consisting of industrial and communal waste 33, wet residues 34 of poor structure and well structured dry residues 35 which are first fed to a comminuting device 36, the respective residues are supplied to the reactor O1 for solid materials separately or in predetermined mixtures, possibly with the addition of air 011 and/or various additives 012.

The solid materials resulting after dewatering from the reactor for solids are fed either as fresh compost or after mixing 38 to a subsequent rotting 39, where they are converted to matured compost 40. Via a discharge 41 the squeezed out liquid fractions after sedimentation are supplied to the anaerobic filter 08 for anaerobic wet fermentation, wherefrom the biogas 42, basically methane, as well as the remaining water 43 are evacuated. Parts of the liquid amounts can also be redirected to the reactor 01 for solid materials as recirculated liquid 44.

In a performed test charge 2 Tons of waste material 33, 34 and 35 from household waste were mixed together in the reactor 01 for solid materials and treated under air supply, whereby a temperature of 72 degrees C was reached. The organic substance in the water 14 squeezed out during the reaction amounted to approximately 23 % of the original weight. Due to the fermentation in the anaerobic reactor 08 approximately 210 m$^3$ biogas 42 with a methane content of 65 % by volume was formed form these organic substances. The active compost was mixed as solid discharge with cut structured material, consisting of bark and brush cuttings, approximately at a ratio of 1:1 and left to lie in a silo without shifting. After that the compost has an earthy smell and was intensively covered by a fungus culture. The obtained compost met the predetermined limit values.

We claim:

1. In a device for the production of biogas and compost through wet fermentation and composting of bio-residuals with a first reactor for solid materials built as a worm-press solid-liquid separator, which has a liquid outlet and a subsequently arranged anaerobic reactor for fermentation with biogas extraction and a composting installation, the improvement wherein the reactor for solid materials has an inclined worm press arranged at an angle, that above and parallel to this worm press a table or table plates are arranged and the reactor for solid materials has a valve for the removal of sediment.

2. The improvement according to claim 1 wherein the reactor has two inclined worm presses operating in opposite directions.

3. The improvement defined in claim 1 wherein the table or table plates are heat exchangers.

4. The improvement defined in claim 3 wherein the first reactor has at least one screen with slotted holes arranged upstream of the outlet of the reactor.

5. The improvement defined in claim 3 wherein the first reactor has a gas evacuation system which is connected to a compost filter.

6. The improvement defined in claim 3 wherein the worm press is arranged in the upper third of the bottom of the reactor and is equipped with an exchangeable slotted hole screen, whose slotted openings run parallel to a conveying direction and/or that the slotted hole screen is at a decreasing distance from the periphery of the rotating worm shaft.

7. The improvement defined in claim 6 wherein the distance between the slotted hole screen and the conveyor worm and the contact pressure can be modified by a changeable suspension of the worm press.

8. The improvement defined in claim 6 wherein the water squeezed out by the worm press is collected and drained off into a collecting basin with an inclined bottom, having a rinsing device.

9. The improvement defined in claim 6 wherein a conveying direction is changed by changing the worm windings above the pressing zone, thereby increasing the compression effect.

10. The improvement defined in claim 6 wherein at the deepest point of a bottom of the reactor bottom there is also an opening which can be closed, for the extraction of the squeezed out water.

11. The improvement defined in claim 6 wherein flexible elements are provided at a margin of the worm shaft for cleaning and prevention of clogging of the openings of the slotted hole screen.

12. The improvement defined in claim 6 wherein a positioning angle of the first reactor and a the bottom inclination thereof, is changeable.

13. The improvement defined in claim 6 wherein the first reactor has a closable filling funnel and a troughed chain conveyor transporting bio-residuals, which are gastight and/or provided with an air exhaust by means of side channel fans.

14. The improvement defined in claim 6 wherein between the first reactor and an anaerobic reactor a sedimentation tank is arranged, which has an outlet through which the resulting sludge can be discharged and directly sent back to the first reactor.

15. The improvement defined in claim 14 wherein the first reactor or the sedimentation tank are provided with an aeration circuit or an air supply system.

16. The improvement defined in claim 14 wherein a degassing reactor, an ultrasound reactor or a biostripper between the sedimentation tank and the anaerobic reactor is provided.

17. The improvement defined in claim 14 wherein the anaerobic reactor is designed as a packed-bed reactor and/or has several grid supports.

18. The improvement defined in claim 17 wherein the grid supports have a rough surface.

19. The improvement defined in claim 14 wherein the anaerobic reactor has a gas dome with a gas separator.

20. The improvement defined in claim 3 wherein several packed-bed reactors as said aerobic reactor are interconnected by communicating pipes.

21. A process for treating organic bioresidues selected from the group which consists of raw and cooked food leftovers, agricultural and animal wastes and plant components, in which said bioresidues have a minimum moisture content of 40% by volume, said process comprising the steps of:

(a) with optional addition of water and recycling of a liquid from an anaerobic reactor, intensively mixing said bioresidues and causing water-soluble organic components contained and formed therein to wash out from said bioresidues and pass into a liquid phase in a resulting mixture;

(b) separating said liquid phase from a solid phase of said residues at least in part by pressing said mixture to express said liquid phase from said solid phase;

(c) subjecting said solid phase after the expression of said liquid phase therefrom to silocomposting;

(d) feeding said liquid phase to said anaerobic reactor and fermenting said liquid phase to produce a biogas; and (e) recovering said biogas from said anaerobic reactor.

22. The process defined in claim 21 wherein a moisture content of substantially 70 to 80% by volume is maintained in the mixture in step (a) while said organic components are washed out of said bioresidues.

23. The process defined in claim 22 wherein a liquid withdrawn from said anaerobic reactor is recycled to step (a).

24. The process defined in claim 23, further comprising the steps of supplying oxygen to said mixture in step (a) and maintaining the temperature in step (a) at a minimum of 70° C.

25. The process defined in claim 24 wherein an exothermic reaction occurs in step (b), further comprising extracting heat produced by exothermic reaction and passing the extracted heat into said anaerobic reactor.

26. The process defined in claim 24 wherein only upon an organic component concentration in said liquid phase separated from said solid phase is residual liquid pressed from said solid phase and said solid phase passed to silocomposting.

27. The process defined in claim 24 wherein the separation in step (b) is carried out by subjecting the mixture to screwpressing against screens.

28. The process defined in claim 24, further comprising the step of sedimenting solids from said liquid phase prior to introducing said liquid phase into said anaerobic reactor.

29. The process defined in claim 28 wherein a sludge formed by sedimentation is introduced into said mixture as an inoculum.

30. The process defined in claim 29, further comprising the step of subjecting said liquid phase to gas stripping to remove oxygen therefrom prior to introducing said liquid phase into said anaerobic reactor.

31. The process defined in claim 24 wherein said liquid phase is subjected in said anaerobic reactor to treatment with mesophilic bacteria at a temperature of 45° to 40° C. and to treatment with thermophilic bacteria at a temperature of 50° to 55° C.

\* \* \* \* \*